United States Patent [19]
Binder et al.

[11] 4,338,175
[45] Jul. 6, 1982

[54] ALL SOLID STATE ELECTRODE SYSTEM

[75] Inventors: Ira Binder, New Rochelle; Horace A. Teass, Jr., Armonk, both of N.Y.

[73] Assignee: McNab, Incorporated, Mount Vernon, N.Y.

[21] Appl. No.: 149,119

[22] Filed: May 12, 1980

Related U.S. Application Data

[63] Continuation-in-part of Ser. No. 22,472, Mar. 21, 1979, abandoned.

[51] Int. Cl.³ .............................................. G01N 27/30
[52] U.S. Cl. .......................... 204/195 R; 204/195 F; 324/438
[58] Field of Search ............... 204/195 R, 195 F, 1 H; 324/438; 128/635

[56] References Cited

U.S. PATENT DOCUMENTS

| | | | |
|---|---|---|---|
| 254,751 | 3/1882 | White et al. | 324/30 R |
| 3,102,085 | 8/1963 | Edwards et al. | 204/290 F X |
| 3,103,481 | 9/1963 | Robinson | 204/195 |
| 3,223,597 | 12/1965 | Hersch | 204/195 R X |
| 3,258,682 | 6/1966 | Maurer | 204/195 R X |
| 4,090,925 | 5/1978 | Jungman | 204/1 T |
| 4,101,403 | 7/1978 | Kita et al. | 204/195 S |
| 4,119,498 | 10/1978 | Edwall et al. | 204/1 T |

FOREIGN PATENT DOCUMENTS

| | | | |
|---|---|---|---|
| 758623 | 5/1953 | Fed. Rep. of Germany | 204/195 F |
| 2328921 | 1/1974 | Fed. Rep. of Germany | 204/195 R |

*Primary Examiner*—G. L. Kaplan
*Attorney, Agent, or Firm*—Peck & Peck

[57] ABSTRACT

A cell body having a pair of electrodes insulated from each other and adapted for direct immersion and use in commercial, laboratory, or industrial fluids or process streams, the cell being usable at temperatures below freezing and above the boiling point of water. The cell includes an insulated ultra pure antimony electrode and an insulated electrode of noble metal, the noble metal of the one electrode being immersed in the process stream as is the pure antimony electrode. The cell provides a self-contained solid state unit with the two electrodes adapted to measure pH in fluids or process streams containing solid mineral or ore particles, in acid, neutral or basic solutions of a wide range of temperatures and pressures, including vacuum applications and this system requires no external or internal reference or standard electrodes. The self-contained all solid-state electrode system is connected directly to the proper electronic circuitry, either nearby or remote to produce a signal or display pH or its equivalent. The pure antimony electrode and its insulation extend into the process stream a further distance than does the noble metal electrode, and the insulation for the noble metal electrode extends beyond the noble metal end thereof.

2 Claims, 4 Drawing Figures

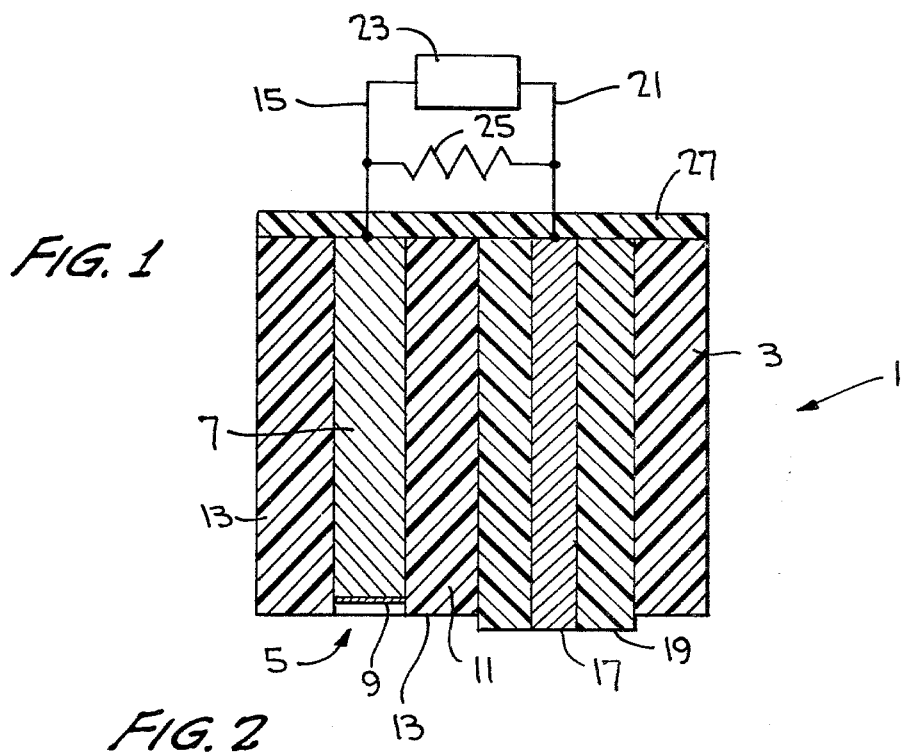
FIG. 1
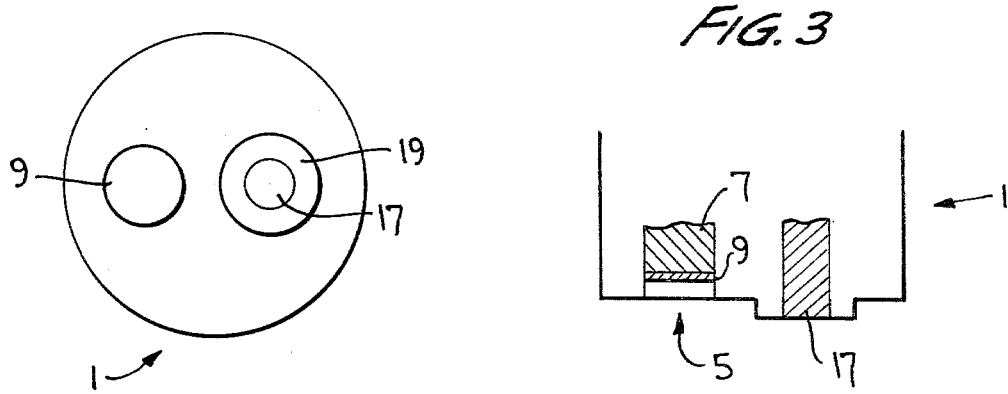
FIG. 2
FIG. 3
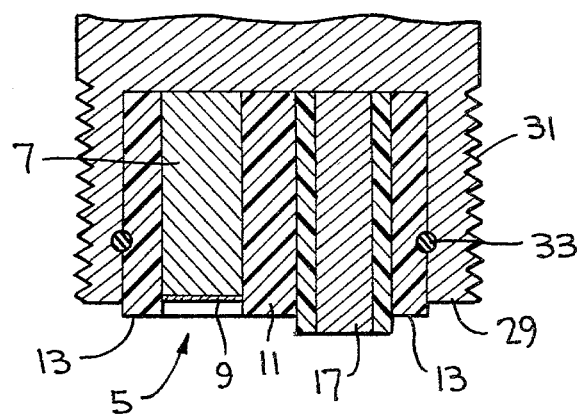
FIG. 4

ALL SOLID STATE ELECTRODE SYSTEM

BRIEF SUMMARY OF THE INVENTION

This application is a Continuation In Part of application Ser. No. 022,472 filed Mar. 21, 1979, and now abandoned.

This invention has been devised with particular thought to overcoming the drawbacks in antimony electrode systems which are now known and in use. It has been our experience that the known antimony electrode systems present problems in use and such problems arise especially in difficult mechanical environments and such problems are often due to the fragile standard reference electrodes which have been required to complete the measurement circuit. Because of these drawbacks in antimony electrode systems such systems have found a limited practical use in industries such as mining and mineral processing, where a rugged, comparatively rapid electrode, which is operable in both acid and alkaline solutions and at moderately high temperatures, is needed to measure pH.

The all-solid state electrode system of this invention overcomes a substantial number of problems which have arisen in the practical use of these systems. This invention presents a simple, reliable, sturdy immersion electrode system and it is significant to appreciate that this system does not require either a standard reference cell or other external reference cell to complete the electronic circuit. It is also of significance that the system of this invention produces a sufficiently large and reproducible output to be read or displayed by proper electronic circuitry. We have connected our simple, self-contained, all-solid state electrode system directly to the proper electronic circuitry, either nearby or remote. It should be understood that this system does not need any liquid, gel or the like. This system provides a self-contained cell with two electrodes, one being formed of ultra pure antimony and the other having a noble metal area for direct contact immersion into the fluid stream. The noble metal is inert and may be platinum or palladium, and this solid state electrode contains no glass or other fragile materials. This self-contained solid state cell having the pure antimony and noble metal electrodes measures pH in fluids which may be acid, neutral or basic solutions of a wide range of process temperatures and pressures, including vacuum applications. The system may be used in laboratory, plant or field applications, may be cleaned or replaced and does not require the preliminary aging or conditioning required by other pH sensing electrodes and standard reference cells.

The system of this invention provides broadly a combination of electrodes, one being all-solid pure antimony while one end of the other is coated with a noble metal, typically platinum or palladium.

In realizing the aims of this invention it is significant to appreciate that the antimony electrode be composed of ultra pure antimony and the reasons for this will become apparent as this description proceeds. Further significance is attached to the constructional characteristic of this system wherein the pure antimony electrode extends a further distance into the fluid stream than does the noble metal coated end of the other electrode, and additionally the end of the insulation surrounding the pure antimony electrode presents a plane surface relative to the operative end of the pure antimony electrode, while the end of the insulation surrounding the noble metal electrode extends beyond the end thereof which is coated with platinum or palladium.

Additional objects and advantages of the present invention will become more readily apparent to those skilled in the art when the following general statements and descriptions are read in the light of the appended drawings.

BRIEF DESCRIPTION OF THE DRAWINGS

FIG. 1 is an elevational view in section of the all-solid state electrode system, dimensions of certain parts being exaggerated for purposes of illustration.

FIG. 2 is a bottom plan view of the all-solid state electrode system of FIG. 1.

FIG. 3 is a side view in section, with parts thereof broken away, particularly illustrating the antimony and noble metal electrodes.

FIG. 4 is a sectional elevational view with parts thereof broken away illustrating a somewhat modified form of the invention.

DETAILED DESCRIPTION OF THE INVENTION

With reference to the accompanying drawings and particularly FIG. 1 thereof the all-solid state electrode system is designated in its entirety by the numeral 1 and comprises a cell body 3 which is formed of insulating material which may be ceramic or plastic and is compatible with the electrodes, which will be described in detail, and with the pH instrumentation. This cell body 3 is preferably of annular configuration for easy insertion into standard piping, connectors, beakers, valves and other sample locating and holding devices. For ease of description we shall term one of the pair of electrodes "the noble metal electrode or reference electrode" and we have designated this electrode generally by the numeral 5. The noble metal electrode 5 consists of a solid brass or the like body 7 which extends from the top of the system and at its lower end is provided with a noble metal surface 9 which, as will become clear as this description proceeds, is adapted to come into contact with the fluid stream being tested. Insulation 11 is provided in addition to the insulation 3 and it is to be noted that the insulation 3 and 11 extend downwardly a distance below the noble metal surface 9 so that such surface is above the bottom surface 13 of the insulation 3 and 11. The electrode is not a so-called usual or "standard reference electrode" but may be termed a "reference electrode" when used in this combination, and is a completely solid state electrode. A "standard reference electrode" is always liquid or gel-filled (calomel; silver/silver chloride; standard hydrogen; and the like). Since the noble metal electrode 5 of this invention has no one of the aforementioned characteristics it is not a "standard reference electrode" as this term is now known and in use in this art. An insulated lead wire 15 is provided which is in electrical contact with the brass or other suitable metal body 7 of the electrode 5, such lead wire 15 provides an electrical connection to the measurement instrumentation. The pure antimony electrode 17 is mounted in a sheath or insulating body 19 which may be formed of ceramic, plastic, epoxy or the like, and the body 19 has a close fit with the cell body 3 and the insulating medium 11 so no liquid leakage will occur. An insulated lead wire 21 is electrically connected at one end to the measurement instrumentation 23 and at the other end to the antimony electrode 17.

The measurement instrumentation 23 is a low impedance measurement instrumentation and 25 comprises an input resistor across the leads 15 and 21. The body 3 of the cell is provided with any suitable type of cap 27 which functions to keep out dirt and other undesired contaminants. It will be evident that the basic construction of the pure antimony electrode is entirely solid state which provides a sturdier electrode which is less subject to breakage or contamination, is usable at high temperatures and pressures and is less subject to problems of impact, shielding or mechanical problems.

The factor of purity in the antimony electrode is not unimportant. The antimony electrode 17 which is used in this system is made from ultra pure, electronics grade antimony, that is, 99.999% antimony. It has been our experience that the purity of the antimony electrode is a factor in the preparation of constant, reproducible antimony pH electrodes. We are aware that antimony (not ultra pure) electrodes have been used in the past, but such use has always been with a standard type, glass enclosed reference electrode, rather than with a noble metal as a solid reference electrode. As far as we are aware no antimony electrode has been heretofore used where the antimony which is used is composed of ultra pure crystals. It is thought that many of the problems encountered in the prior art may have originated in the lack of the use of raw material purity. It should also be appreciated that the utilization in this particular combination of ultra pure antimony provides a different response than is provided when antimony of less purity is employed. With the utilization of the aforementioned ultra pure antimony, the pH response is more stable and more reproducible.

It will be appreciated that the noble metal end 9 on the base metal 7 is a thin layer so that it becomes necessary to have the insulator 11 extend beyond the noble metal end 9 of the noble metal electrode 7. This particular construction is followed not only for sealing purposes but to insure that only the noble metal surface 9 is exposed to the test solution. If this constructional course was not followed the material would be changed, and therefore, the response to the noble metal reference electrode. Additionally, it has been our experience that at infrequent intervals the pure antimony electrode 17 must be cleaned by gentle polishing and thus the pure antimony electrode is formed to project slightly beyond the major insulating body 3 for ease of cleanup and polishing. Since the polishing and cleaning action required is gentle and very little surface material is actually removed the amount of such projection can be on the order of 1 or 2 millimeters. It is exceedingly undesirable to polish or scratch the very thin surface layer 9 of the noble metal electrode which serves as the reference electrode and this constitutes yet a further reason for having the insulation 11 extend beyond the noble metal surface. The above discussed dimensional characteristics are exaggerated in the drawings for purposes of illustration.

In use the entire cell body including both the pure antimony electrode and the inert noble metal electrode is placed into the fluid or process stream to be measured and is then connected as explained to the measurement instrumentation 23. The system is then ready for testing or measurements and it must be appreciated that no usual standard or reference cell of the type described above is necessary, nor is any aging or prior conditioning of the electrodes required. The pH instrumentation 23 and the associated components can be designed to provide direct readings in millivolts, pH units and the like. It is to be understood that this system has been designed so that the components thereof are accessible for inspection, maintenance and replacement.

In use of the electrode system and the circuitry the pure antimony electrode 17 is connected to the resistor 25 and the meter 23 through conductor 7. Similarly, the noble metal electrode 5 is connected to conductor 7 which is typically formed of brass, to the opposite side of meter 23 and register 25 through the conductor 15. The noble metal electrode and its conductor 7 are isolated from the antimony electrode 17 by insulating materials 13 and 19. Pure antimony electrode 17 and the noble metal electrode 5 are introduced into the liquid to be measured, it is to be noted that only the noble metal surface 9 of the noble metal electrode 5 comes into contact with the liquid. Thus, the electrical path is completed and across the junction a voltage is produced proportional to the pH.

In FIG. 4 of the drawings a modified form of this invention is disclosed. The modified form of the all-solid state electrode system is adapted for use where higher pressures occur. In the description of this modified form of the invention the same reference numerals have been used in FIG. 1 for parts which are similar. The outer portion 29 of the cell functions as a holder and it may be composed of plastic, ceramic, metal or coated metal materials. The outer circumferential surface of the outer portion 29 is threaded as at 31 so that it may be inserted into standard threaded piping, valves or connectors. It must be appreciated that the choice of materials for the outer portion 29 may vary widely with the temperature, pressure and chemical makeup of the fluid to be tested. If desired, an O-ring 33 may be used between the outer portion 29 and the insulating medium 13.

What is claimed is:

1. An all solid state electrode system for the measurement of the pH of a fluid stream including a cell body having a metalloid electrode composed of ultra-pure antimony combined with an insulated from an electrode of a noble metal of the platinum group of metals, said noble metal electrode being a reference electrode which is inert to chemical attack by the fluid stream of which the pH is being measured, said noble metal electrode having a body portion formed of a conducting material and a noble metal on and covering an end thereof and in contact with said body portion, the noble metal covered end of said noble metal electrode and said metalloid electrode being immersed in the fluid stream, leads connecting each electrode to low impedance electronic pH instrumentation, and an input resistor connected across said leads, the electrical path being completed and a voltage being produced proportional to the pH in the fluid stream for displaying on the electric low impedance pH instrumentation the measurement of the pH in the field stream, said metalloid electrode being composed of electronics antimony of 99.999% purity.

2. An all solid state electrode system in accordance with claim 1, wherein said two electrodes are insulated one from the other and said insulation is formed providing a sheath completely surrounding each electrode, said pure antimony electrode extending into said fluid stream a greater distance than said noble metal electrode and the insulation surrounding said noble metal electrode extending beyond the noble metal end thereof.

* * * * *